United States Patent [19]
Rehmann

[11] Patent Number: 5,324,293
[45] Date of Patent: Jun. 28, 1994

[54] SURGICAL BROACH AND BROACH HOLDER

[75] Inventor: Mark L. Rehmann, Pflugerville, Tex.

[73] Assignee: U.S. Medical Products, Inc., Austin, Tex.

[21] Appl. No.: 975,808

[22] Filed: Nov. 13, 1992

[51] Int. Cl.$^5$ .................... A61B 17/00; A61F 2/32
[52] U.S. Cl. ........................................ 606/85; 606/99
[58] Field of Search ............... 606/85, 86, 87, 88, 606/79, 84, 80, 176, 91, 99, 100, 104; 623/16, 23

[56] References Cited

U.S. PATENT DOCUMENTS

| | | | |
|---|---|---|---|
| 4,583,270 | 4/1986 | Kenna | 606/85 |
| 4,601,289 | 7/1986 | Chiarizzio | 606/85 |
| 4,765,328 | 8/1988 | Keller | 606/85 |
| 4,990,149 | 2/1991 | Fallin | 606/85 |
| 5,064,427 | 11/1991 | Burkinshaw | 606/99 |
| 5,089,003 | 2/1992 | Fallin | 606/85 |
| 5,190,550 | 3/1993 | Miller | 606/85 |

OTHER PUBLICATIONS

Intermedics Orthopedics, APR Hip System Surgical Procedure May 1988, pp. 22–23.
Intermedics Orthopedics, Inc. Premier Total Hip System, 1988, brochure #1000-01-600.
Orthomet, Inc. Minn, MN, Perfect Hip System Product Brochure.
Zimmer, Inc. Macrofit Hip System Brochure, 1986, #97-6540-001-00.
Osteomcs Corp. Allendale, N.J., 1989 Surgical Protocall, Omniflex Lit. #LSP-20.
Biomet, Inc. Warsaw Ind., 1992, Bio-groove Brochure, #Y-BMI-221/013192.
DePuy, Warsaw, Ind., Gemini Total Hip System Brochure, 1988, #0601-42 Rev 1.
Exactech, Inc., Gainesville, Fla., Cemented Total Hip System, Catalog/Brochure.

*Primary Examiner*—Michael A. Brown
*Attorney, Agent, or Firm*—Shaffer & Culbertson

[57] ABSTRACT

An apparatus for holding a surgical broach during a surgical broaching procedure comprises a handle body with a handle bearing surface formed on one end of the body, an elastically deformable link member, and a loading arrangement connected to the handle body. The loading arrangement is adapted to apply a tensile connecting force on the link member and the link member is adapted to apply the connecting force to the broach to be connected to the handle. The connecting force applied to the broach by the link member pulls the broach toward the handle body with the handle bearing surface mating with a corresponding bearing surface formed on the broach. The broach includes a latch surface by which the connecting force is applied to the broach with the link member.

8 Claims, 3 Drawing Sheets

SURGICAL BROACH AND BROACH HOLDER

BACKGROUND OF THE INVENTION

This invention is directed to a surgical broaching tool or broach and an apparatus for holding a broach during a surgical broaching procedure, and particularly to a broach holding apparatus that can securely but releasably hold broaches of a variety of sizes. The invention also encompasses a method of securely but releasably holding a surgical broach.

Some orthopedic implantation procedures require a step of preparing an opening in a patient's bone for receiving an implant. Hip replacement surgery or arthroplasty, for example, requires the step of producing a longitudinal opening in the patient's femur for receiving a stem portion of a femoral prosthetic implant. The step of producing the opening includes first boring an initial opening and then impacting progressively larger sizes of broaching instruments or broaches into the opening until producing the desired shape for receiving the implant stem. A broach holding tool or instrument is connected to each broach and used to apply the impact required to insert and remove the broach.

Substantial impact to the broach is required to insert the broach into the femoral canal, and then withdraw the broach. The connection between the broach and broach holding tool therefore must be very secure. Yet is desirable that the broach be easily releasable from the broach holder so that a single broach holder can be used with several different broaches of different sizes and shapes. Also, it is desirable to use the fully seated final size broach as a guide for planing the upper surface of the femur and as a trail implant stem for verifying certain aspects of the artificial joint to be produced. The broach holder must be adapted to release from the broach in order to employ the inserted broach as a femur planning guide and trial stem. Finally, the broach holder must reconnect to the inserted broach in order to remove the broach from the femur.

SUMMARY OF THE INVENTION

It is therefore an object of the invention to provide a broach holding apparatus adapted to securely hold surgical broaches in a wide range of sizes but to release easily without having to apply substantial force to the broach. Another object of the invention is to provide a surgical broach adapted to be used with the new broach holding apparatus. It is also an object of the invention to provide a method for securely but releasably holding broaches in a broad range of sizes with a single broach holding tool.

In order to accomplish these objects, a broach holding apparatus or instrument according to the invention is adapted to pull a broach tightly against a bearing surface formed on the apparatus and to maintain the pulling or connecting force to maintain a secure yet releasable connection between the broach holding apparatus and the broach. Since the apparatus makes the connection with the broach by applying a pulling force between the holding tool and broach, the broach is readily releasable and a single broach holder can be used with virtually any sized broach.

A broach holder according to the invention includes a handle body having a shape suitable for manipulating a broach connected thereto and for applying to the broach the force or impact required during the surgical broaching procedure. The handle body includes a handle bearing surface that preferably forms a v-shape adapted to mate with a corresponding bearing surface formed on the broach used with the holder. Elastically deformable link means associated with the handle body applies the connecting force to the broach, pulling the broach bearing surface tightly against the handle bearing surface to make a secure connection between the handle and broach. The holder apparatus also includes loading means connected to the handle body for loading the connecting force on the link means and maintaining the connecting force to keep the broach securely connected to the holder.

The loading means preferably comprises a lever pivotally connected at one end to the handle body. The link means preferably comprises an elongated arcuately shaped member pivotally connected to the lever and made from an elastically deformable material. The end of the link member opposite the end connected to the lever includes a hook-shaped catch surface adapted to catch on a corresponding latch surface formed on the broach. The connecting force is applied to the broach through the catch surface hooked or caught on the latch surface of the broach.

To connect the broach to the broach holder, the hook-shaped catch surface is first hooked on the latch surface formed on the broach. Next, the lever is pivoted to draw the link member and the now loosely connected broach toward the handle body. Once the handle bearing surface is mated with the broach bearing surface, pivoting the lever further loads the connecting force on the link, thereby elastically deforming the link. Pivoting the lever past a line extending through the catch point and the lever pivot point causes the force loaded on the link member to pull the lever tightly against the handle body. The lever thus holds the connecting force on the link member and keeps the broach securely connected to the handle body. Releasing the broach, however, involves simply pulling the lever in the opposite direction past the line extending through the catch point and lever pivot point, allowing the tension on the link member to release, and then unhooking the catch surface on the link from the latch surface on the broach.

A single broach holder according to the invention can be used with virtually any sized broach having the corresponding bearing surface and latch surface. This eliminates the need to have several different broach holders to accommodate the different broach sizes needed to perform a broaching operation. Also, the connecting structure can be released easily and quickly without having to apply substantial force to the broach.

These and other objects, advantages, and features of the invention will be apparent from the following description of the preferred embodiments, considered along with the accompanying drawings.

DESCRIPTION OF THE PREFERRED-EMBODIMENTS

Figure 1:
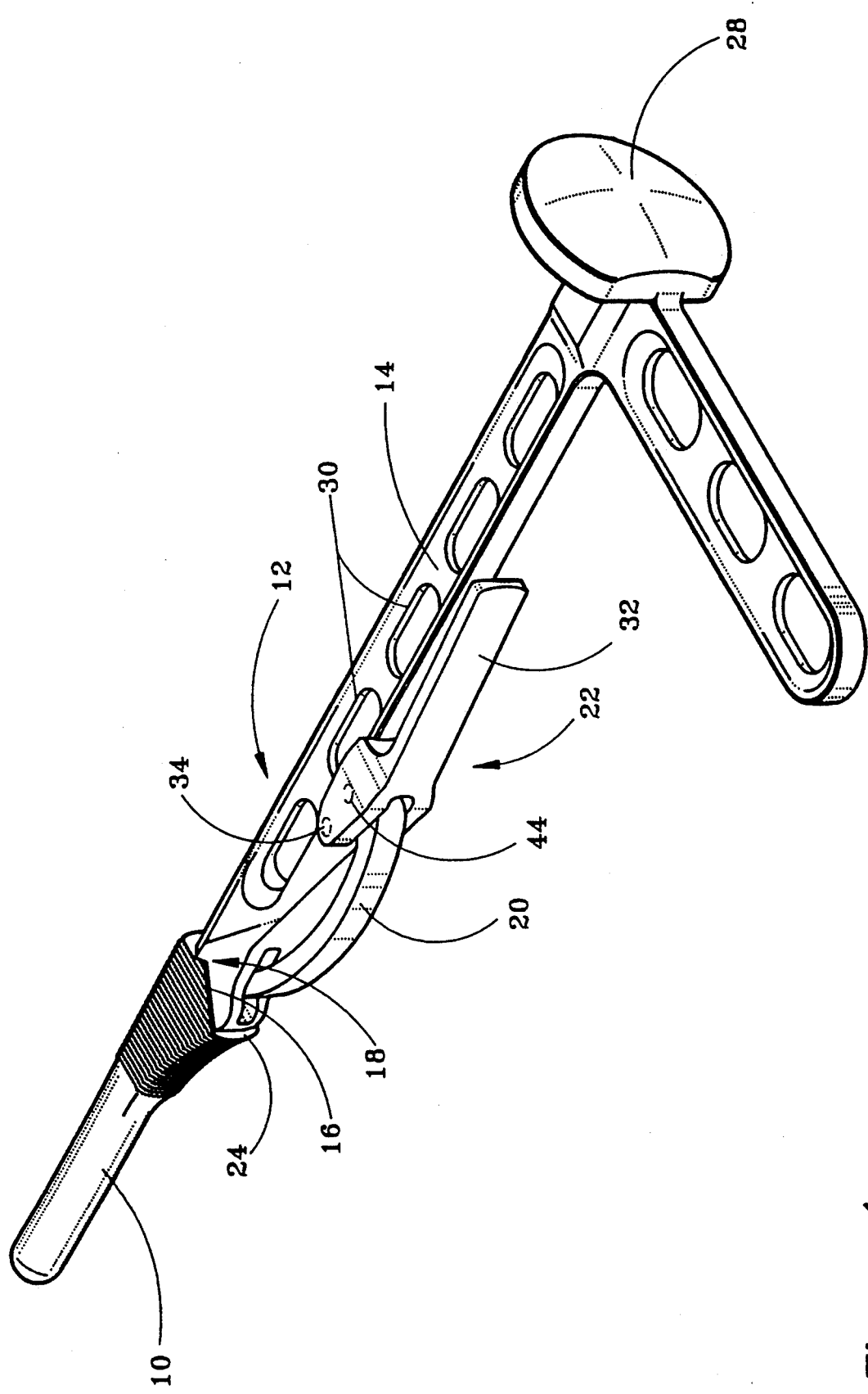
FIG. 1 is a view in perspective of a broach holding apparatus and broach embodying the principles of the invention.
Figure 2:
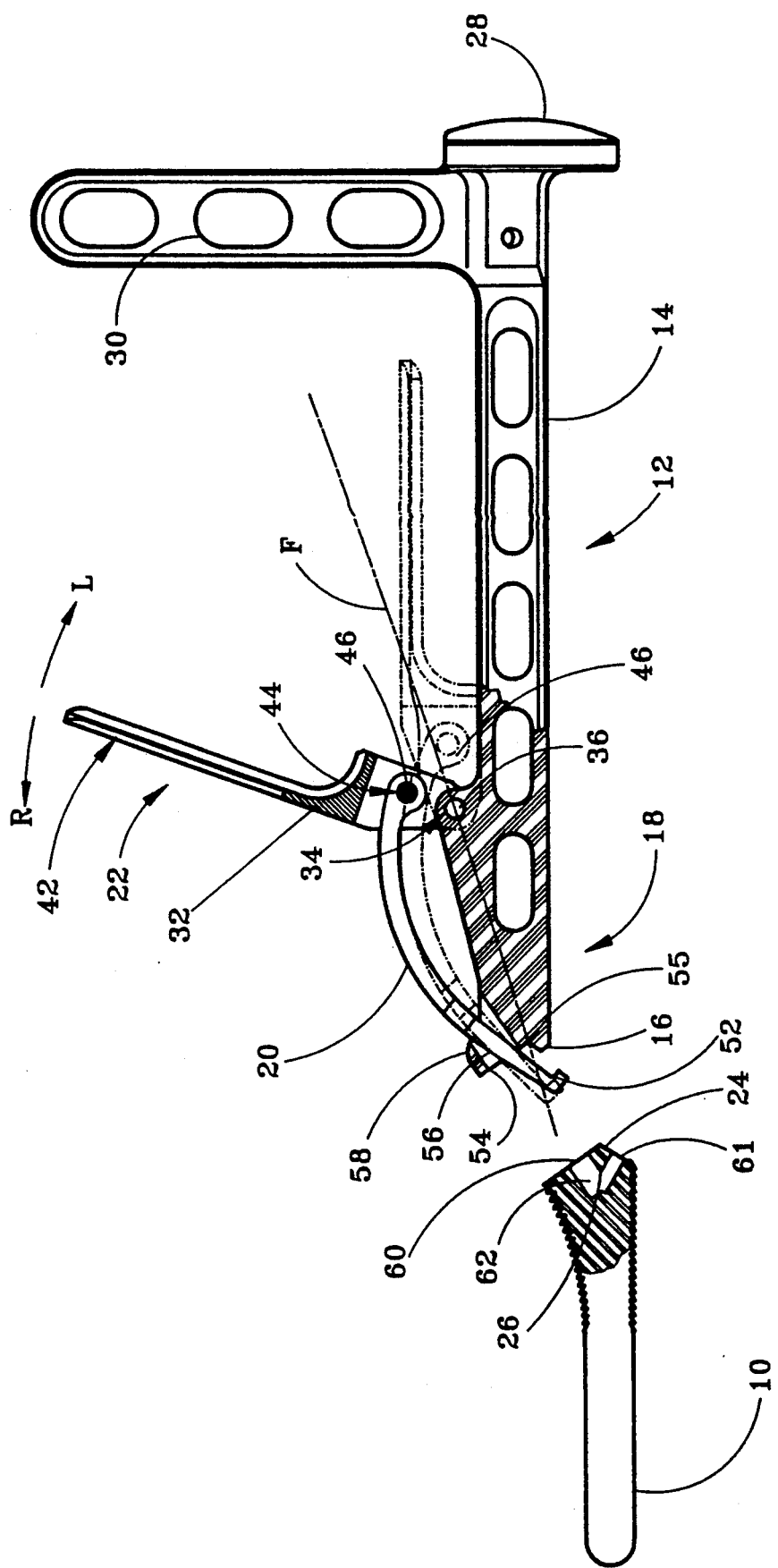
FIG. 2 is a partial longitudinal section view of the broach holder apparatus and broach shown in FIG. 1, but with the broach released, and the lever shown in the locked position in phantom.
Figure 3:
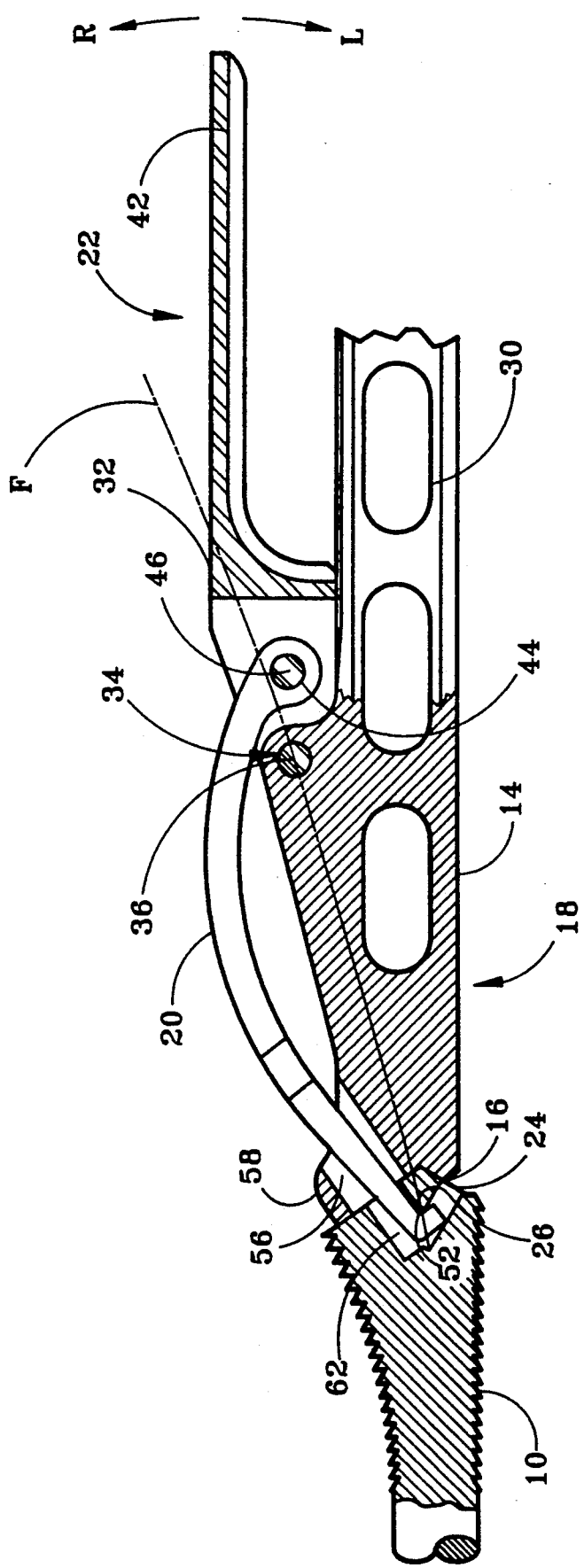
FIG. 3 is a partial longitudinal section view similar to FIG. 2, but with the broach connected as in FIG. 1.

FIGS. 1 through 3 show one preferred form of broach 10 and broach holder 12 embodying the principles of the invention. The illustrated broach 10 and broach holder 12 are specifically designed for use in hip arthroplasty. As shown best in FIGS. 2 and 3, the broach holder 12 includes a handle body 14 with a handle bearing surface 16 formed at a broach holding end 18 of the handle body, link means 20, and loading means 22. The broach 10 includes a bearing surface 24 formed on an end of the broach to be connected to the holder 12. FIGS. 2 and 3 illustrate that the broach 10 also includes a latch corner 26 or other surface for co-operating with the link means 20.

The handle body 14 is made from any suitable rigid material and has a shape that allows the surgeon to apply the forces required to insert the broach 10 into the patient's bone (not shown) and then withdraw the broach when required. An impacting surface 28 is preferably formed at the end of the handle body opposite the broach holding end 18. Also, the handle body 14 includes a series of openings 30 strategically placed to lighten the handle body without reducing its strength and rigidity. Although the illustrated handle body is preferred, those skilled in the art will readily appreciate that any desired handle configuration could incorporate the broach connecting structure embodying the principles of the invention.

The link means 20 and loading means 22 in this form of the invention are positioned near the broach holding end 18 of the handle body 14. The loading means 22 comprises a lever 32 pivotally connected to the handle body at pivot connection 34. Although any suitable pivot connection may be used, the preferred pivot connection 34 includes a precision shaft 36 inserted in aligned openings through the lever 32 and through the handle body 14. The opposite end of the lever 32 includes a grip section 42. Referring particularly to FIGS. 2 and 3, the lever 32 is adapted to pivot about the pivot connection 34 in the directions indicated by arrows L and R.

The link means 20 comprises an elongated member made of an elastically deformable material. One end of the link means or member 20 is pivotally connected to the lever 32 at pivot connection 44. Similarly to the pivot connection 34, the pivot connection 44 between the link member 20 and lever 32 preferably comprises a precision shaft 46 extending through aligned openings through the link member and the lever. The elongated arcuate shape of the link member 20 and its elastic properties allows the member to elastically straighten under a tensile force applied at either end thereof. Also, a catch surface 52 is formed at the end of the link member 20 opposite the end connected to the lever 32. In the illustrated form of the invention the catch surface 52 comprises generally a hook-shaped section.

As shown in FIG. 2 the bearing surface 16 formed on the broach holding end 18 of the handle body 14 preferably comprises two surfaces 54 and 55 lying in two different planes which intersect to form generally a v-shape. The end of the link member 20 with the catch surface 52 formed thereon extends through an opening 56 in the handle body 14 and is positioned adjacent to the broach holding end 18 of the handle. The opening 56 is closed with member 58 and forms link positioning means to maintain the catch portion 52 of the link member 20 adjacent to the broach holding end 18 of the handle even when a broach is not connected.

The broach 10 is made of any suitable rigid material and the broach bearing surface 24 is located at the end of the broach adapted to connect to the handle body 14. The broach bearing surface 24 has a shape corresponding to, and adapted to mate with, the handle bearing surface 16. As shown best in FIG. 2, the broach bearing surface 24 in this form of the invention, includes two discrete surfaces 60 and 61 lying in two planes which intersect to form a v-shape corresponding to the v-shaped handle bearing surface 16. The broach latch corner 26 or other suitable surface for receiving the link catch portion 52 is positioned on the broach body preferably near the end of the broach to be connected to the handle body 14. In this form of the invention the broach latch corner 26 is formed within the broach body and an opening 62 through the broach bearing surface 24 provides access to the latch corner.

Although the structures for the broach 10 and broach holder 12 shown in FIGS. 1 through 3 are preferred, those skilled in the art will readily appreciate that a number of modifications may be made to both the broach holder and the broach within the scope of the invention. For example, other types of levers or other arrangements may be employed as the loading means to apply the connecting force to the link member. Also, the link member may have a number of other configurations or may comprise other types of elastically deformable structures. Furthermore, the handle bearing surface 16 and broach bearing surface 24 may comprise any suitable surfaces adapted to securely mate together when the connecting force is applied between the handle body 14 and broach 10 by the link member 20. For example, a plurality of v-shaped surfaces may be employed or the v-shape may be aligned along a different axis than that shown in the figures.

The method of releasably connecting a broach and broach holder according to the invention can be described with particular reference to FIGS. 2 and 3. The method includes first loading a connecting force on the elastically deformable link member 20. This loading step is performed with the loading means 22, in the illustrated form of the invention the lever 32. The method further includes applying the connecting force to the broach 10 with the link member 20 so that the connecting force pulls the bearing surface 24 formed on the broach tightly against the bearing surface 16 formed on the handle body 14. Finally, the method includes maintaining the connecting force on the link member 20 with the loading means 22.

The broach connecting method is performed in the illustrated form of the invention by pivoting the lever 32 first away from the handle body 14 to extend the catch surface 52 or other suitable arrangement formed on the link member 20. With the link member catch portion 52 extended, it may catch on the corresponding latch corner 26 formed on the broach body as shown in FIG. 2. From this point the step of loading the connecting force on the link member 20 comprises pivoting the lever 32 toward the handle body 14 in the direction of arrow L. This pivoting movement pulls the catch surface 52 on the link member 20 relatively closer to the handle body 14 until the handle body bearing surface 16 and the broach bearing surface 24 abut. At the point where the handle bearing surface 16 and the broach bearing surface 24 come together, further rotation of the lever 32 toward the handle body 14 loads a tensile force on the link member 20 and causes the link member to elongate elastically. The step of applying the connecting force to the broach is performed by the elastically elongated or loaded link member 20 connected at one end to the lever 32 with the other end having the catch surface 52 caught on the latch corner 26 formed on the broach body.

The step of maintaining the connecting force with the loading means 22 is performed by cooperation between the lever 32 and the handle body 14 and the position of the line of force between the lever pivot 34 and the point at which the link member 20 catches on the broach body latch corner 26. When the lever 32 is first pivoted toward the handle body 14 to load a force on the link member 20, the force on the link member tends to pull the lever in direction of arrow R in FIG. 2. However, once the lever 32 is pivoted toward the handle body 14 past the line F extending through the lever pivot 34 and the point at which the link member 20 applies force to broach, the force loaded on the link member pulls the lever in the opposite direction (direction L) until the lever contacts the handle and can not pivot further as shown in FIG. 3. At this point, the broach 10 is securely connected to the holder 12 and the holder may be used to apply the required impacting force to insert and remove the broach.

To release the broach 10 either after the broach has been removed from the patient's bone or while seated in the bone, the operator need only pivot the lever 32 in the direction of arrow R in FIG. 2. Pivoting the lever in direction R first unloads the link member 20 to release the connecting force and then moves the catch surface 52 of the link member relatively further away from the handle bearing surface 16 so that the catch surface may be unhooked from the latch corner 26 formed on the broach 10. Thus, the broach 10 releases very easily and without having to apply any substantial force to the broach.

The above described preferred embodiments are intended to illustrate the principles of the invention, but not to limit the scope of the invention. Various other embodiments and modifications to these preferred embodiments may be made by those skilled in the art without departing from the scope of the following claims.

I claim:

1. An apparatus for holding a surgical broach during a surgical broaching procedure, the apparatus comprising:
    (a) a handle body;
    (b) a handle bearing surface formed on a broach holding end of the handle body, the handle bearing surface being adapted to mate with a corresponding bearing surface formed on a surgical broach when the broach is in a broaching position with respect to the handle body;
    (c) an elastically deformable link member having a catch surface formed thereon and adapted to catch on a latch corner formed on the broach, the link member for catching on the latch corner of the broach to apply a connecting force between the broach and the handle body when the broach is in the broaching position, and elongating elastically in response to the connecting force; and
    (d) an elongated loading member pivotally connected to the handle body and to the link member for loading and maintaining the connecting force on the link member so that the link member holds the broach in the broaching position with respect to the handle body.

2. The apparatus of claim 1 wherein:
    (a) the link member has an arcuate shape such that a tensile force applied at either end thereof elastically straightens the link member.

3. The apparatus of claim 1 further comprising:
    (a) link positioning means connected to the handle body for maintaining the end of the link member that is not connected to the lever positioned in an area adjacent to the handle bearing surface.

4. The apparatus of claim 1 wherein:
    (a) the handle bearing surface includes a first surface lying in a first plane and a second surface lying in a second plane, the first and second planes intersecting to form generally a v-shape and each intersecting a longitudinal axis of the handle body at an acute angle.

5. The apparatus of claim 1 wherein:
    (a) the handle bearing surface includes a plurality of discrete surfaces, each discrete surface lying in a different plane and the planes intersecting to form a plurality of v-shapes, and each plane intersecting a longitudinal axis of the handle body at an acute angle.

6. In a surgical tool holding apparatus having a handle body by which a surgical tool may be manipulated during a surgical procedure, the improvement comprising:
    (a) an elastically deformable link member having a catch surface formed thereon and adapted to catch on a latch corner formed on the surgical tool, the link member for catching on the latch corner of the surgical tool to apply a connecting force between the surgical tool and the handle body when the tool is in a connected position in which a bearing surface formed on the surgical tool mates with a bearing surface formed on the handle body, and for elongating elastically in response to the connecting force; and
    (b) an elongated loading member pivotally connected to the handle body and to the link member for loading and maintaining the connecting force on the link member so that the link member holds the broach in the broaching position.

7. The surgical tool holding apparatus of claim 6 wherein the link member comprises:
    (a) an elongated member having an arcuate shape such that a tensile force applied to either end thereof elastically straightens the arcuately shaped elongated member.

8. The surgical tool holding apparatus of claim 6 wherein the handle bearing surface comprises:
    (a) at least one pair of opposing bearing surfaces, each surface of the pair lying in a substantially different plane which intersects a longitudinal axis of the handle body at an acute angle, and the planes intersecting to form substantially a v-shape.

* * * * *